United States Patent [19]

Diez

[11] Patent Number: 5,681,313
[45] Date of Patent: Oct. 28, 1997

[54] DEVICE FOR THE EXTENSION OF BONES

[75] Inventor: Ingolf Diez, Muehlheim, Germany

[73] Assignee: Karl Leibinger Medizintechnik GmbH & Co. KG, Muehleim/Donau, Germany

[21] Appl. No.: 592,215

[22] Filed: Jan. 26, 1996

[30] Foreign Application Priority Data

Feb. 6, 1995 [DE] Germany ............... 295 01 880.1

[51] Int. Cl.⁶ .................................................. A61B 17/58
[52] U.S. Cl. .............................. 606/69; 606/70; 606/71
[58] Field of Search ............................ 606/69, 70, 71, 606/57, 105, 86, 87, 55, 96, 60, 63; 433/173

[56] References Cited

U.S. PATENT DOCUMENTS

| 4,187,841 | 2/1980 | Knutson | 606/57 |
| 4,906,189 | 3/1990 | Knapp | 433/173 |
| 5,122,140 | 6/1992 | Asche et al. | 606/55 |

FOREIGN PATENT DOCUMENTS

| 8807909 | 10/1988 | Germany. | |
| 335797 | 3/1959 | Switzerland | 606/71 |
| 627580 | 8/1949 | United Kingdom | 606/71 |

OTHER PUBLICATIONS

Dtsch Z Mund Kiefer Gesichts Chir 18, 236 (1994).

*Primary Examiner*—Michael Buiz
*Assistant Examiner*—Julian W. Woo
*Attorney, Agent, or Firm*—Dilworth & Barrese

[57] ABSTRACT

The invention relates to a device for bone extension comprising two bone plates adapted to be slid in relation to one another in the longitudinal direction. In accordance with the invention one bone plate is designed in the form of a slide, which is adapted to slide bidimensionally in relation to the other bone plate.

15 Claims, 2 Drawing Sheets

DEVICE FOR THE EXTENSION OF BONES

BACKGROUND OF THE INVENTION

The invention relates to a device for the extension of bones comprising two boneplates adapted to slide in relation to one another in the longitudinal direction.

In corrective surgery bone extension devices are frequently employed in order to compensate for false positioning and deformities. More particularly such devices are employed on the upper and lower extremities. Another field of application is the use of suitable bone extension devices for the extension of the jaw. Devices so far employed in this area operate using an extension device, which is applied externally. The danger with such systems is that microbes may be introduced along the pins into the interior of the body and cause infections.

In Dtsch Z Mund Kiefer GesichtsChir 18, 236 (1994) a traction device is described for the left lower jaw, which possesses a miniature angular bone plate for fixation to the ascending limb of the lower jaw and a T-shaped bone plate for fixation to the horizontal lower jaw. This device is applied internally and may be extended to the required degree by an extension screw driver. Using this device extension of the jaw is only possible in one direction, namely in the longitudinal direction of the device.

A further device, with which bone extension is possible is disclosed in the German utility model 8,807,909. In this case as well however extension is only possible in one direction in space.

Particularly in the case of extension of the jaw bone there is however the problem that bidimensional correction is necessary.

SUMMARY OF INVENTION

One object of the invention is consequently to so develop the known extension device that bidimensional bone correction becomes possible.

In accordance with the invention this aim is achieved starting with the device of the type initially mentioned for extension of bones comprising two bone plates adapted to slide in relation to each other in the longitudinal direction and using the following features. In accordance with such features one of the two bone plates is designed in the form of a slide, which is able to be slid bidimensionally in relation to the other bone plate along a curved track.

Preferred developments of the invention will be seen from the dependent claims. In accordance therewith sliding of the two bone plates in relation to one another may be by means of a lead screw. The same is preferably arranged rotatably in a longitudinal slot in an extension of the one bone plate. A nut runs on the lead screw and articulates with a thrust plate, which for its part is connected with the slide constituting the second bone plate.

At least during a part of the sliding movement the slide preferably has a pin thereof running in a groove, suitably defining the curved track, in the other bone plate. The curved track or cam is selected in accordance with medical requirements.

Preferably the lead screw is able to be adjusted by means of a spring wire shaft mounted on it. The spring wire shaft can preferably emerge from the gum so that the appropriate setting may be undertaken by the patient him- or herself at given intervals, as for example every day in the mouth cavity.

BRIEF DESCRIPTION OF THE DRAWINGS

Further features and advantages of the invention will be gathered from a working embodiment shown in detail in the drawings, in which.

DESCRIPTION OF THE PREFERRED EMBODIMENT(S)

Figure 1:
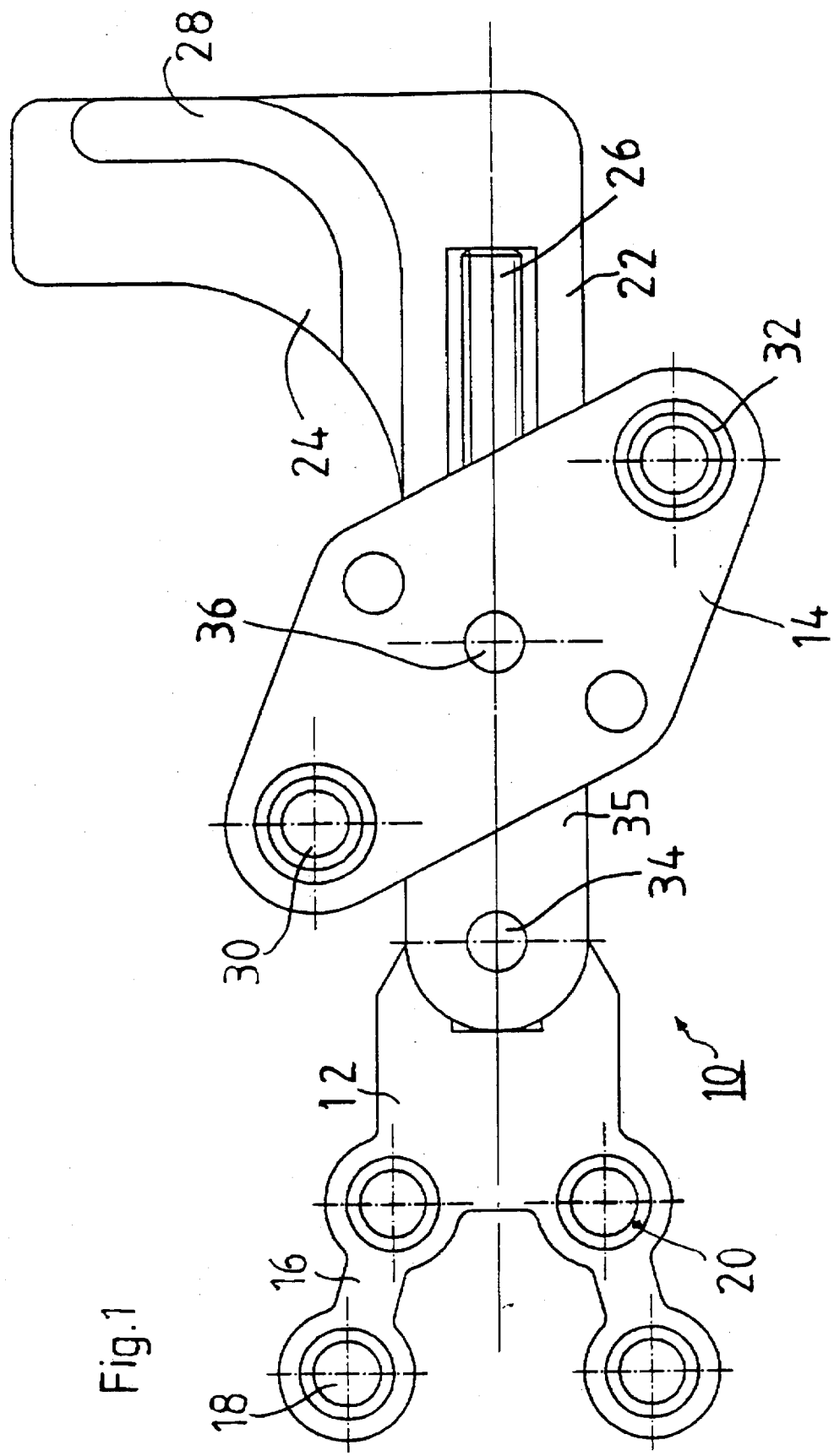
FIG. 1 shows an embodiment of the device in accordance with the invention in its initial setting, i.e. in the contracted setting.

The embodiment of the invention illustrated in FIG. 1 constitutes a bone extension device 10 forming one possible structure in accordance with the present invention. The extension device has as its main parts a first bone plate 12 and a second bone plate 14, which is arranged to slide in relation to it and is in the form of a slide.

In the present embodiment the bone plate 12 comprises two arms 16 each having two screw threaded holes 18 each. The borders of the holes 18 are slanted. Such slant is indicated at 20. For locking onto a bone, as for instance the lower jaw bone, countersunk head bone screws, which are of known design and hence not shown here in detail, are screwed into such screw holes. Opposite the arms 16 an L-shaped extension 22 and 24 is formed on the bone plate 12. In the longer limb of the L-shaped extension, which is placed centrally in relation to the two arms 16, as illustrated in FIG. 1, a lead screw 26 is rotatably arranged in a longitudinal slot. A spring wire shaft runs through the bone plate 12 in a manner not illustrated here and is connected with the lead screw for the transmission of torque. Using such a spring wire shaft, which after the bone plate has been screwed in place is passed through the gum into the mouth, it is possible for the lead screw 26 to be turned to the required degree.

A nut, not illustrated in FIG. 1 in detail, screwingly engages the lead screw 26. A bolt 34 is formed on the nut and constitutes the articulating connection with one end of a thrust plate 35. The other end of the thrust plate 35 is rotatably connected via a screw threaded bolt 36 with the bone plate 14 embodied in the form of a slide. The bone plate 14 has the form of a slightly distorted rhomb with rounded corners. Two holes 30 are provided for corresponding bone screws. On the edges of the holes 30 there are again slanting surfaces 32 to accommodate the countersunk heads of the bone screws.

In the shorter limb 24 of the L-shaped extension of the bone plate 12 a groove 28 is cut to form a cam or curved track. The curved configuration of the groove 28 is adapted to medical requirements as regards displacement of the jaw bone. In the working embodiment here considered only one particular configuration is illustrated. The form of the curve or cam could also be steeper or less steep. If appropriate the short arm of the L-shaped extension of the bone plate 12 would be made wider.

Figure 2:
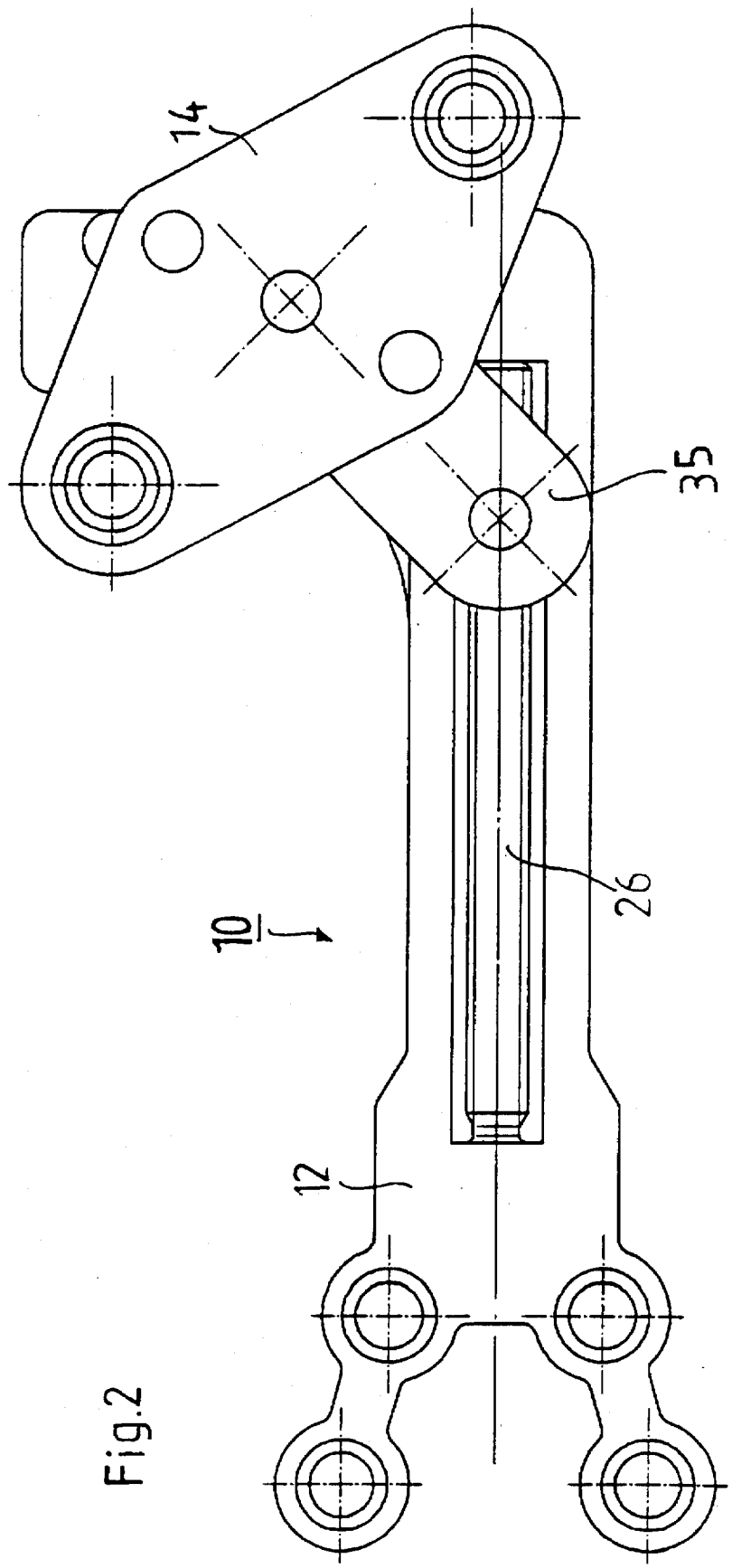
FIG. 2 shows the device of figure in its extended setting.

A pin formed on the bone plate 14, which is designed in the form of a slide, runs in the groove, the pin not being depicted in FIGS. 1 and 2 in detail. In this case the bone plate 14 is positively guided by means of the pin in the groove 28 with the result that both the thrust plate 35 and also the bone plate 14 are tilted on further turning of the lead screw 26. This will be apparent from the showing of FIG. 2. In this case the device 10 is illustrated in its extended terminal setting. Accordingly the jaw bone may be corrected in a simple manner bidirectionally.

I claim:

1. An internal fixation device for the extension of bones comprising two bone plates articulatingly connected and adapted to slide in relation to each other in the longitudinal direction, wherein one such bone plate is designed in the form of a slide, which is able to be slid along a curved track in the longitudinal direction in relation to the other bone plate bidimensionally.

2. The device as claimed in claim 1, where in sliding of the two bone plates in relation to each other takes place using a screw.

3. A device for the extension of bones comprising two bone plates adapted to slide in relation to each other in the longitudinal direction wherein one such bone plate is designed in the form of is slide, which is able to be slid along a curved track in the longitudinal direction in relation to the other bone plate bidimensionally, sliding of the two bone plates in relation to each other takes place using a screw, and the screw is arranged in a rotatable fashion in a longitudinal slot in an extension of the other bone plate and using the screw, a thrust plate, which is connected articulatingly with a bolt, may be caused to slide, said thrust plate being for its part articulatingly connected with the slide.

4. The device as claimed in any claim 1 wherein at least in the course of one part of the sliding movement the slide has a pin thereof fitting into a corresponding groove in the other bone plate, said groove defining said curved track.

5. A device for the extension of bones comprising two bone plates adapted to slide in relation to each other in the longitudinal direction, wherein one such bone plate is designed in the form of a slide, which is able to be slid along a curved track in the longitudinal direction in relation to the other bone plate bidimensionally, and sliding of the two bone plates in relation to each other takes place using a screw.

6. The device as claimed in claim 2, wherein at least in the course of one part of the sliding movement the slide has a pin thereof fitting into a corresponding groove in the other bone plate, said groove defining said curved track.

7. A device for the extension of bones comprising two bone plates adapted to slide in relation to each other in the longitudinal direction, wherein one such bone plate is designed in the form of a slide, which is able to be slid along a curved track in the longitudinal direction in relation to the other bone plate bidimensionally, sliding of the two bone plates in relation to each other takes place using a screw, the screw is arranged in a rotatable fashion in a longitudinal slot in an extension of the other bone plate and using the screw, a thrust plate, which is connected articulatingly with a bolt, may be caused to slide, said thrust plate being for its part articulatingly connected with a slide, and at least in the course of one part of the sliding movement the slide has a pin thereof fitting in to a corresponding groove in the other bone plate, said groove defining said curved track.

8. The device as claimed in claim 1, wherein all components thereof are structured and arranged for internal fixation and extension of bones of a jaw.

9. The device as claimed in claim 1, whereto said one bone plate is in the form of a slightly distorted rhomb with rounded corners.

10. The device as claimed in claim 2, wherein said one bone plate is in the form of a slightly distorted rhomb with rounded corners.

11. The device as claimed in claim 3, wherein said one bone plate is in the form of a slightly distorted rhomb with rounded corners.

12. The device as claimed in claim 4, wherein said one bone plate is in the form of a slightly distorted rhomb with rounded corners.

13. The device as claimed in claim 6, wherein said one bone plate is in the form of a slightly distorted rhomb with rounded corners.

14. The device as claimed in claim 2, wherein said screw extends in the longitudinal sliding direction.

15. The device as claimed in claim 6, wherein said screw extends in the longitudinal sliding direction.

* * * * *